(12) United States Patent
Mihashi et al.

(10) Patent No.: US 8,490,839 B2
(45) Date of Patent: Jul. 23, 2013

(54) FILTERING DISPENSER CONTAINER

(75) Inventors: Hirokazu Mihashi, Kameoka (JP); Seiji Yoshimura, Ibaraki (JP); Kazuko Suzuki, Ibaraki (JP); Yorihisa Uetake, Nagoya (JP); Norio Hoshi, Nagaokakyo (JP); Shinji Matsuda, Nagoya (JP); Hidetoshi Kondo, Kiyosu (JP)

(73) Assignees: Taisei Kako Co., Ltd. (JP); Nihon Tenganyaku Kenkyusyo Co., Ltd. (JP)

( * ) Notice: Subject to any disclaimer, the term of this patent is extended or adjusted under 35 U.S.C. 154(b) by 140 days.

(21) Appl. No.: 12/995,736

(22) PCT Filed: May 21, 2009

(86) PCT No.: PCT/JP2009/059340
§ 371 (c)(1),
(2), (4) Date: Feb. 17, 2011

(87) PCT Pub. No.: WO2009/147952
PCT Pub. Date: Dec. 10, 2009

(65) Prior Publication Data
US 2011/0144598 A1    Jun. 16, 2011

(30) Foreign Application Priority Data
Jun. 3, 2008 (JP) .................................. 2008-146209

(51) Int. Cl.
*B67D 7/76* (2010.01)
(52) U.S. Cl.
USPC ....................................... 222/189.06; 222/494
(58) Field of Classification Search
USPC ......... 222/189.06, 189.09, 95, 105, 212–215, 222/420, 422, 490, 494, 545–546, 481.5
See application file for complete search history.

(56) References Cited

U.S. PATENT DOCUMENTS

| 4,136,693 | A  | * | 1/1979  | Dyke ............................ 604/126 |
| 4,372,306 | A  | * | 2/1983  | Genese et al. ................. 604/122 |
| 6,030,632 | A  | * | 2/2000  | Sawan et al. .................. 424/405 |
| 6,142,343 | A  | * | 11/2000 | Wade et al. .................... 222/182 |
| 6,207,052 | B1 | * | 3/2001  | Webb ........................ 210/321.75 |
| 6,336,571 | B1 | * | 1/2002  | Chibret et al. ............ 222/189.09 |
| 6,649,121 | B1 | * | 11/2003 | Hamamoto et al. .......... 264/513 |
| 6,672,479 | B2 | * | 1/2004  | Shiraishi et al. .............. 222/105 |
| 6,708,850 | B2 | * | 3/2004  | Uetake et al. ............ 222/189.06 |
| 7,867,434 | B2 | * | 1/2011  | Iwahashi et al. .............. 264/513 |
| 7,967,983 | B2 | * | 6/2011  | Grevin ..................... 210/321.75 |
| 7,971,753 | B2 | * | 7/2011  | Mihashi et al. ................. 222/95 |
| 7,971,755 | B2 | * | 7/2011  | Faurie ....................... 222/189.09 |
| 8,056,766 | B2 | * | 11/2011 | Grevin ..................... 222/189.06 |

(Continued)

*Primary Examiner* — Kevin P Shaver
*Assistant Examiner* — Christopher Luzecky
(74) *Attorney, Agent, or Firm* — Wood, Phillips, Katz, Clark & Mortimer

(57) ABSTRACT

In a filtering dispenser container which includes a plug attached to a mouth portion of a bottle thereof and having a liquid discharge passage, and a filter and a check valve provided in the discharge passage, air lock is prevented, even if the container contains a highly percolative liquid, by preventing a very small amount of liquid percolating the check valve from reaching the filter. In the filtering dispenser container, a dam (14) is provided between the check valve (23) and the filter (25) for retaining a very small amount of the liquid percolating the check valve (23) when the check valve is closed. Thus, the filter (25) is prevented from being wetted with the liquid percolating the closed check valve (23) during storage or delivery of the container before the first use of the container.

10 Claims, 9 Drawing Sheets

U.S. PATENT DOCUMENTS

| | | | |
|---|---|---|---|
| 8,118,183 B2 * | 2/2012 | Iwahashi et al. | 215/12.2 |
| 2002/0130139 A1 * | 9/2002 | Shiraishi et al. | 222/105 |
| 2002/0153386 A1 * | 10/2002 | Uetake et al. | 222/1 |
| 2004/0074925 A1 * | 4/2004 | Faurie | 222/212 |
| 2005/0139611 A1 * | 6/2005 | Kubo et al. | 222/189.06 |
| 2007/0028988 A1 * | 2/2007 | Mihashi et al. | 139/383 A |

* cited by examiner

FILTERING DISPENSER CONTAINER

TECHNICAL FIELD

The present invention relates to a filtering dispenser container which can be advantageously used as a liquid container such as an eyedropper container.

BACKGROUND ART

The applicant of the present invention has been developing eyedropper containers capable of maintaining an aseptic environment therein without the use of a preservative, and the resulting accomplishments are disclosed in the following patent literatures 1 to 4.

CITATION LIST

Patent Literatures

PLT1: JP-A-2004-262470
PLT2: JP-A-2003-276719
PLT3: JP-A-2002-263166
PLT4: JP-A-2002-80055

These prior-art aseptic eyedropper containers disclosed each include a laminate bottle including a squeeze-deformable outer layer and an inner layer provided on an inner surface of the outer layer and delaminatable from the outer layer, and a plug provided at a mouth portion of the bottle and having an discharge passage through which a content liquid is discharged from a body of the inner layer. A check valve and a hydrophilic filter are provided in the discharge passage of the bottle. The check valve includes a valve flange, a valve head and a connector sleeve integrally formed of an elastic material such as silicone rubber. The valve head includes an orifice provided at the center thereof and having a cross-shaped incision. The connector sleeve has a flexible structure having a smaller thickness for easy deformation. Therefore, when the outer layer is squeeze-deformed to increase the pressure in the body of the inner layer, the check valve is elastically deformed to shift the valve head downstream to open the orifice. Thus, the content liquid flows downstream through the filter to be dispensed dropwise. Before the first use of the eyedropper container, the liquid is not present in a space between the check valve and the filter, so that the filter is dry. After the first use, the space between the check valve and the filter is filled with the liquid.

SUMMARY OF INVENTION

Technical Problem

Some eye liquids to be contained in the bottle are highly percolative due to addition of a synthetic surface active agent. In this case, even if the orifice of the check valve is normally closed, a very small amount of the liquid percolates the incision to flow out toward the filter during storage or delivery of the container before the first use of the container.

If the hydrophilic filter absorbs the liquid, however, air is trapped in the space between the check valve and the filter, i.e., so-called air lock occurs, because the air cannot pass through the filter. This makes it substantially impossible to dispense the liquid dropwise.

It is therefore an object of the present invention to prevent the air lock, even if the highly percolative liquid is contained in the container, by preventing a very small amount of the liquid percolating the check valve from reaching the filter.

Solution to Problem

To achieve the above object, the present invention has the following technical features.

According to the present invention, there is provided a filtering dispenser container including: a bottle having a body which contains a liquid, and a mouth portion through which the liquid is discharged from the body; a plug attached to the mouth portion of the bottle, the plug having an discharge passage through which the liquid is discharged from the body of the bottle, the plug including a filter and a check valve provided in the discharge passage, the filter being disposed downstream of the check valve with respect to a liquid discharging direction; and a dam provided between the check valve and the filter for retaining the liquid percolating through the check valve kept closed.

Even if a very small amount of the liquid flows out of the body to percolate the closed check valve in the inventive filtering dispenser container during storage or delivery of the container before the first use of the container, the dam retains the very small amount of the liquid to prevent the liquid from being absorbed by the filter. This prevents the air lock, which may otherwise occur when the filter absorbs the liquid before the first use.

In the inventive filtering dispenser container, the plug further includes a spacer disposed between the check valve and the filter, and the spacer keeps the check valve and the filter a predetermined distance away from each other. Further, the dam is provided in the spacer. With this arrangement, the spacer prevents the filter from being wetted before the first use, while providing a space sufficient for the operation of the check valve.

The dam may be a groove which opens toward the check valve. With this arrangement, the very small amount of the liquid percolating the closed check valve can easily flow into the dam, and flow out of the dam away from the filter. This prevents the filter from being wetted even if the bottle is repeatedly toppled and erected.

The discharge passage has a guide groove provided between the check valve and the dam in an inner peripheral wall thereof for guiding the liquid percolating the closed check valve toward the dam. With this arrangement, when the liquid percolating the closed check valve flows on the inner peripheral wall of the discharge passage toward the filter, the liquid can be forcibly guided into the dam. Thus, the filter is more reliably prevented from being wetted.

The inventive dispenser container may further include a plurality of ribs radially provided between the check valve and the filter. The dam may be provided in the ribs, and liquid flow holes may be defined between the ribs. With this arrangement, the liquid flow holes ensure smooth flow of the liquid when the dispenser container is used as intended.

The inventive dispenser container may further include a damper wall provided between the check valve and the body in the mouth portion. The damper wall may have a liquid flow hole. With this arrangement, the damper wall damps the flow of the liquid flowing therethrough. When the dispenser container is toppled, for example, the damper wall prevents the pressure of the liquid in the body from acting on the check valve at a dash. This prevents leakage of the liquid from the check valve.

In the inventive filtering dispenser container, the plug includes a tubular base liquid-tightly engaged with the mouth portion of the bottle, a nozzle cap liquid-tightly fitted around the base and having a liquid outlet port provided at a top thereof, and a tubular spacer fitted in the base downstream of the check valve with respect to the liquid discharging direction, the check valve being retained in the base, the filter being disposed between the top of the nozzle cap and the spacer. The dam is provided in the spacer, and the spacer includes a liquid flow hole through which the liquid flows toward the filter after passing through the check valve when the check valve is open. With this arrangement, the dispenser container has a structure that ensures easy assembling, and yet is capable of preventing the filter from being wetted because the very small amount of the liquid percolating the closed check valve is retained in the dam before the first use. The liquid flow hole of the spacer permits the liquid to smoothly flow toward the filter when the dispenser container is used as intended.

The spacer may have a guide groove provided in an inner peripheral wall thereof for guiding the liquid percolating the closed check valve to the dam. With this arrangement, when the liquid percolating the closed check valve flows on the inner peripheral wall of the spacer toward the filter, the liquid can be forcibly guided into the dam. Thus, the filter is more reliably prevented from being wetted.

The spacer may have a plurality of ribs radially provided at an end thereof adjacent to the filter. Further, the dam may be provided in the ribs, and liquid flow holes may be defined between the ribs.

The base includes a damper wall disposed between the check valve and the body in the mouth portion. The damper wall has a liquid flow hole, and damps the flow of the liquid flowing therethrough. With this arrangement, the liquid flowing through the damper wall is damped by the damper wall. When the dispenser container is toppled, for example, the damper wall prevents the pressure of the liquid in the body from acting on the check valve at a dash. This prevents leakage of the liquid from the check valve.

The plug attached to the mouth portion of the inventive dispenser container has a discharge passage through which the liquid is discharged out of the body of the bottle. A check valve for opening and closing the discharge passage of the plug is provided in the discharge passage, and includes a valve flange and a valve head. Preferably, the valve flange and the valve head are connected to each other via a valve sleeve having a flexible structure. The valve flange seals an inner peripheral edge of the discharge passage. The valve head is preferably connected to an inner peripheral edge of the valve flange directly or indirectly via the valve sleeve or the like. The valve head preferably has an orifice which is opened to permit the liquid to flow when a predetermined dispensing pressure acts on the inside of the bag, and closed to block the flow of the liquid when the predetermined dispensing pressure is removed.

Advantageous Effects of Invention

According to the present invention, the dam is provided between the check valve and the filter for retaining the very small amount of the liquid percolating the closed check valve, whereby the filter is prevented from being wetted with the liquid percolating the closed check valve during the storage or the delivery of the container before the first use of the container. This prevents the air lock.

DESCRIPTION OF EMBODIMENTS

Figure 1:
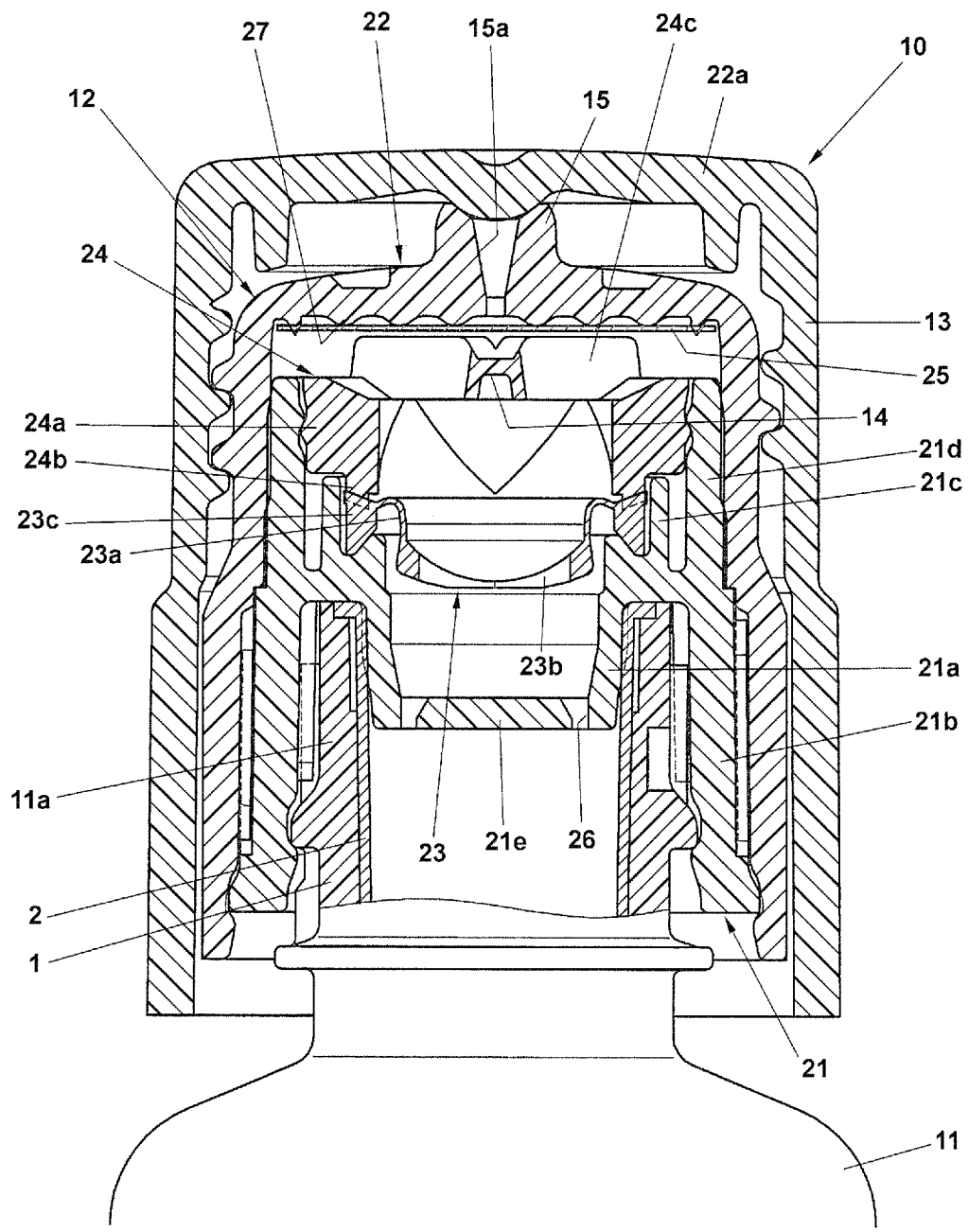
FIG. 1 is an enlarged sectional view showing the structure of a mouth portion of a filtering dispenser container according to one embodiment of the present invention.
Figure 2:
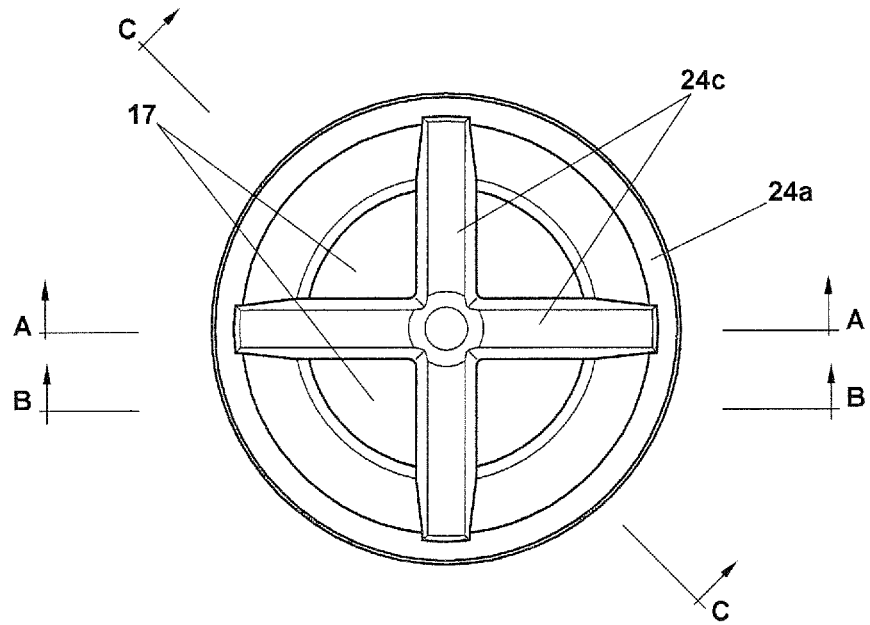
FIG. 2 is a plan view of a spacer of the container.
Figure 3:
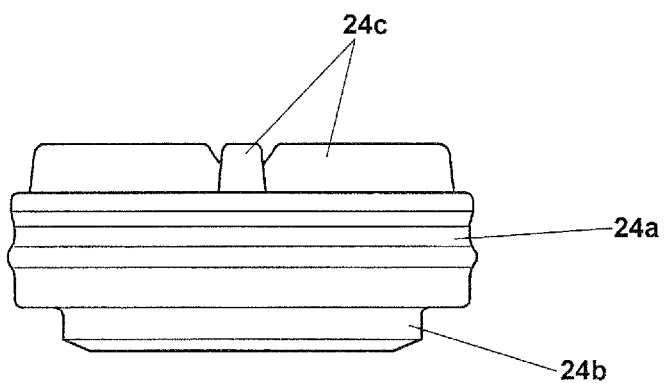
FIG. 3 is a front view of the spacer of the container.
Figure 4:
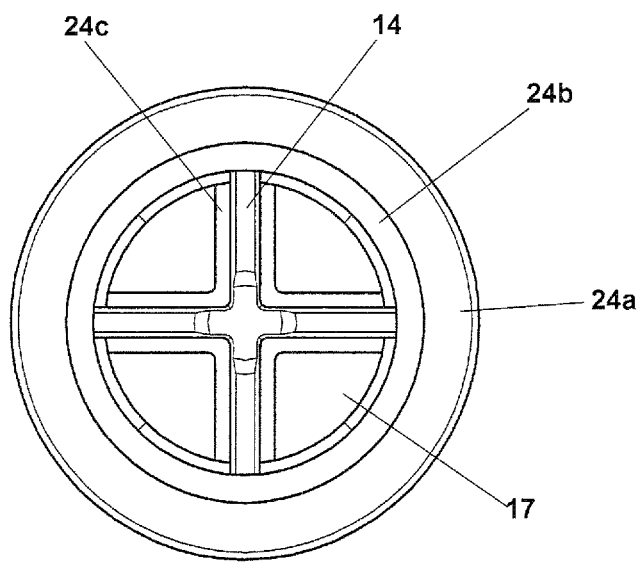
FIG. 4 is a bottom view of the spacer of the container.
Figure 5:
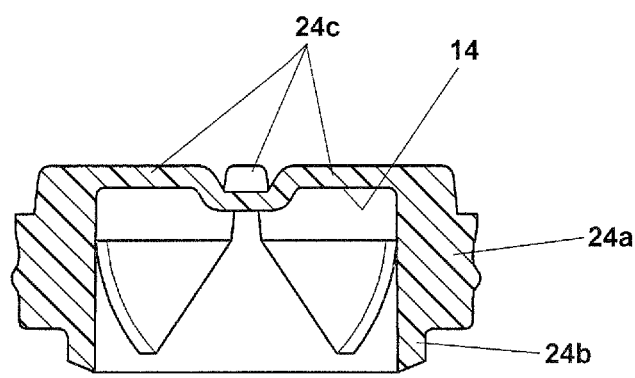
FIG. 5 is a sectional view taken along a line A-A in FIG. 2.
Figure 6:
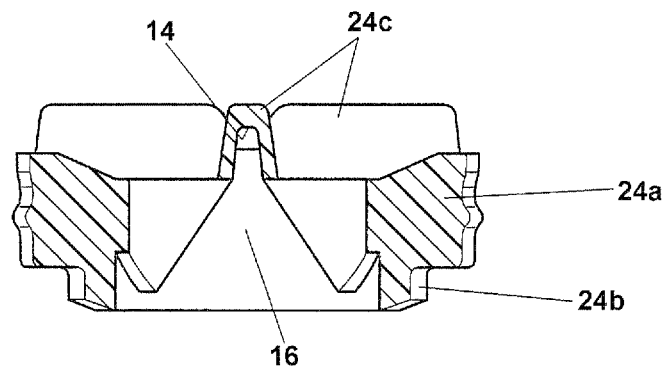
FIG. 6 is a sectional view taken along a line B-B in FIG. 2.
Figure 7:
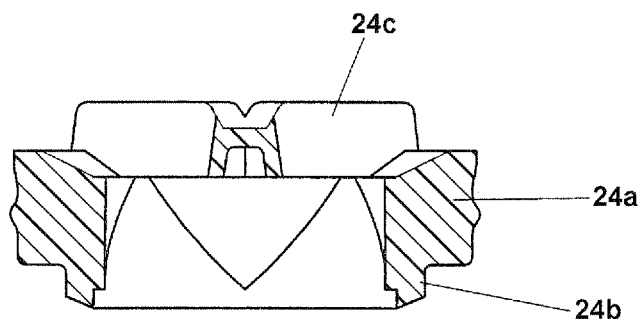
FIG. 7 is a sectional view taken along a line C-C in FIG. 2.
Figure 8:
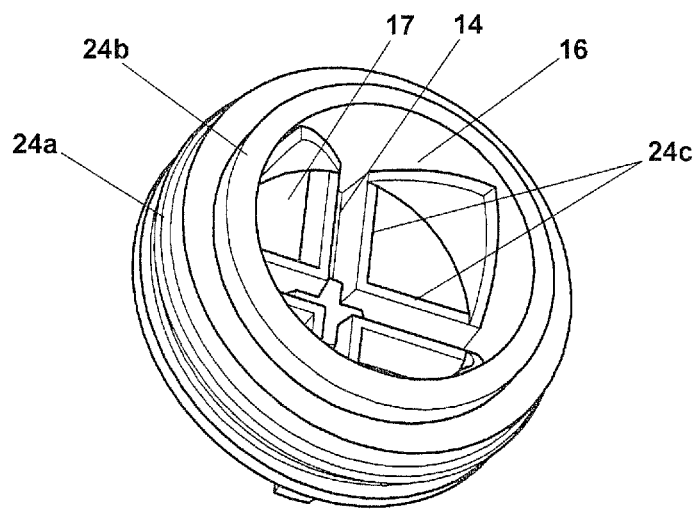
FIG. 8 is a perspective view of the spacer.

FIG. 1 illustrates an eyedropper container 10, as a filtering dispenser container according to one embodiment of the present invention, which includes a delaminatable laminate bottle. The eyedropper 10 includes a delaminatable laminate bottle 11 of a double layer structure including an inner layer and an outer layer, a plug 12 attached to a mouth portion 11a of the bottle 11, and a protection cap 13. When a user removes the cap 13 and holds the laminate bottle 11 upside down to press and squeeze a body 11b of the laminate bottle 11, an eye liquid (fluid) flows out of the bottle 11 through an discharge passage in the plug 12 to be thereby dropped from a distal nozzle portion 15.

The laminate bottle 11 has a laminate structure which includes an outer layer bottle 1 (squeeze bottle) defined as the outer layer and an inner layer bag 2 (fluid containing bag) defined as the inner layer. The details of the laminate bottle are the same as those disclosed in the prior art literatures described above. The outer layer bottle has a cylindrical mouth portion, and a body having a flat cross section. The outer layer bottle is composed of a synthetic resin such as PET or EVOH, and the inner layer bag is composed of a synthetic resin (e.g., a polyolefin such as polyethylene) which permits easy delamination from the outer layer bottle.

Figure 9:
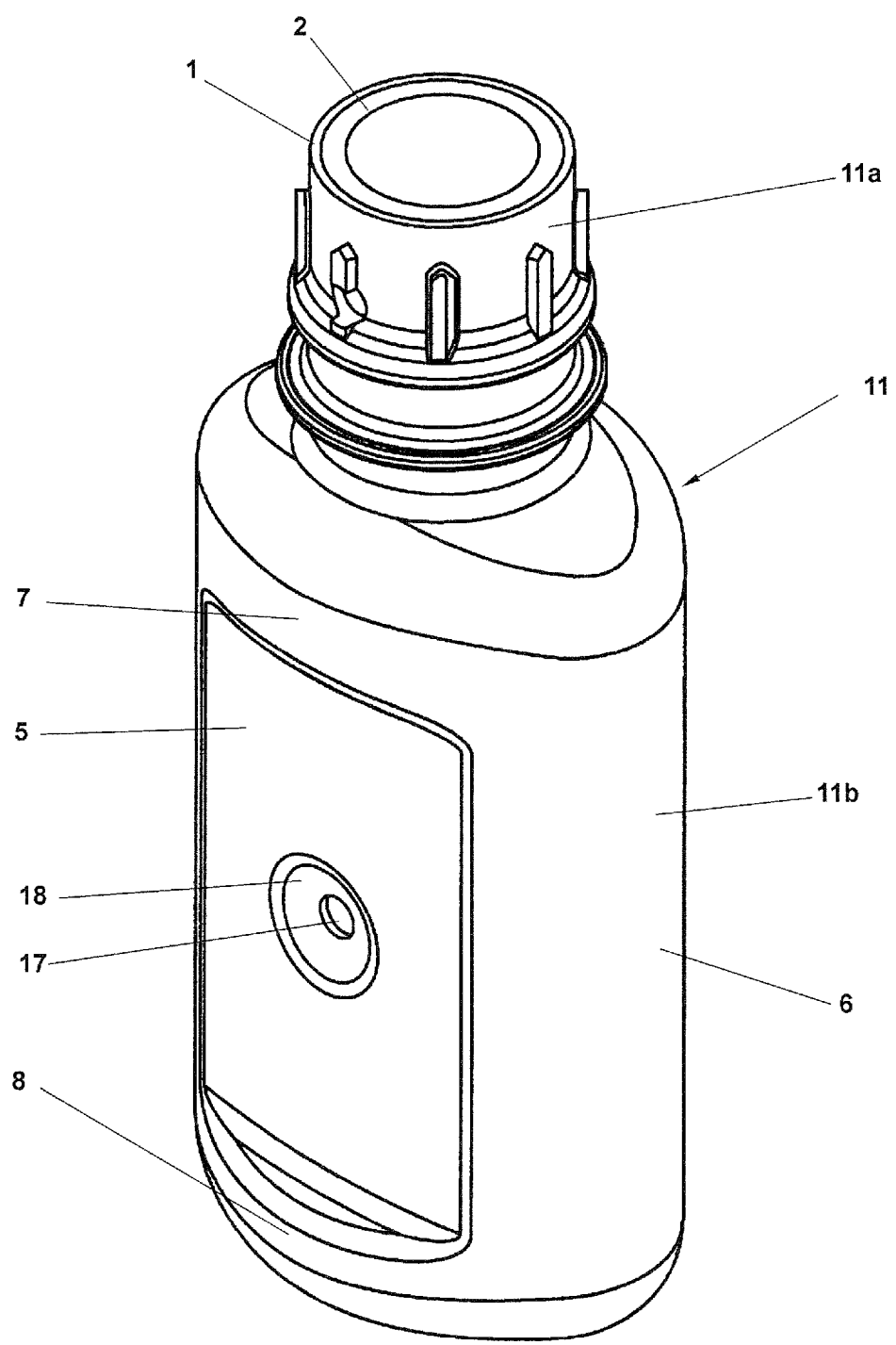
FIG. 9 is a perspective view of a bottle of the container.

As also shown in FIG. 9, the outer layer bottle is configured such that the cylindrical mouth portion is connected to an upper end of the elastically squeeze-deformable bottomed tubular body via a shoulder portion having a diameter progressively decreasing toward its upper end. The body has a flat oval peripheral wall which includes front and rear rigid wall portions 5 spaced a predetermined distance in opposed relation, and left and right flexible connection wall portions 6 respectively connecting left and right edges of the front rigid wall portion 5 to left and right edges of the rear rigid wall portion 5, and has an anteroposterior thickness which is smaller than a lateral width thereof. The rigid wall portions 5 (front and rear wall portions) each have a vertically elongated rectangular shape as viewed from the front side, and are generally planar in cross section and vertical section. The cross section and the vertical section are not necessarily required to be completely planar, but may be slightly curved. The flexible connection wall portions 6 (left and right wall portions) each have an arcuate shape with an anteroposteriorly middle portion thereof projecting laterally outward, and each have a curvature radius that is smaller than the length of the minor axis of the body. Upper edges of the rigid wall portions 5 are connected to the shoulder portion via a flexible upper connection portion 7, and lower edges of the rigid wall portions 5 are connected to a bottom portion of the body via a flexible lower connection portion 8.

When vertically middle portions of the front and rear rigid wall portions 5 of the outer layer bottle having the aforesaid construction are pressed by two fingers to be displaced toward each other to positions spaced a distance that is one half the original distance between the middle portions, the left and right connection wall portions 6 and the upper and lower connection portions 7, 8 are deformable within a resiliently deformable range so that the upper and lower edges of the rigid wall portions 5 follow the displacement of the middle portions.

In this embodiment, the front rigid wall portion 5 (front wall portion) of the outer layer bottle has an introduction hole 17 provided in a vertically and transversely middle portion thereof for introducing outside air into a space between the body of the outer layer bottle and a body of the inner layer bag. The introduction hole 17 extends through the outer layer bottle from the inside to the outside of the outer layer bottle, but the inner layer bag has no introduction hole. Further, the rigid wall portion 5 has a round recess 18 provided in the vertically and transversely middle portion thereof and having a greater diameter than the introduction hole 17. The recess 18 is indented inward of the bottle, and the diameter thereof is about 5 mm. The introduction hole 17 is provided in the recess 18. The introduction hole 17 can be closed by closing the recess 18 by a finger. The introduction hole 17 has no check valve and, hence, is always open. The introduction hole has an opening area of about 1 mm$^2$ to about 2 mm$^2$. The body of the inner layer bag is in a film form and, therefore, is easily deformable to shrink as the amount of the content liquid is reduced.

The plug 12 mainly includes a tubular base 21 liquid-tightly engaged with the mouth portion of the bottle, a nozzle cap 22 liquid-tightly fitted around the base 21 and having a liquid outlet port 15a provided at a top thereof, a check valve 23 retained in the base 21 and capable of being opened and closed, a tubular spacer 24 fitted in the base 21 downstream of the check valve 23 with respect to a liquid discharging direction, and a hydrophilic filter 25 provided between a top plate 22a of the nozzle cap 22 and the spacer 24.

Figure 11:
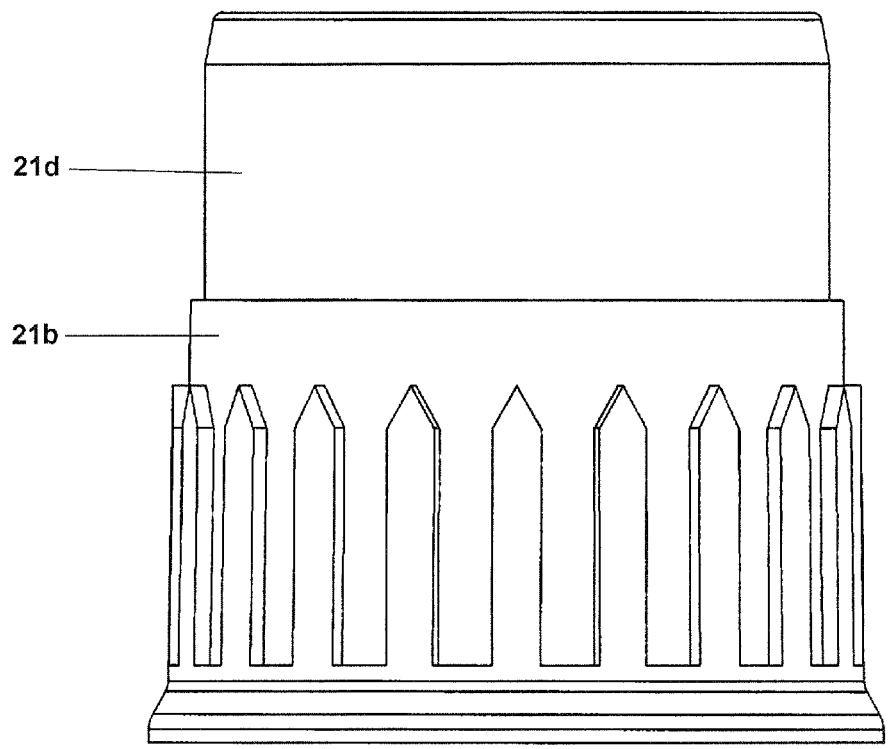
FIG. 11 is a front view of the base of the container.

As also shown in FIG. 11, the base 21 integrally includes a first tubular portion 21a liquid-tightly fitted in the bottle mouth portion 11a from an open end of the bottle mouth portion 11a, a second tubular portion 21b fitted around the bottle mouth portion 11a, a third tubular portion 21c retaining the check valve 23 therein, and a fourth tubular portion 21d in which the spacer 24 is fitted. The first and second tubular portions 21a, 21b radially overlap each other below the open end of the bottle mouth portion 11a, and the third and fourth tubular portions 21c, 21d radially overlap each other above the open end of the bottle mouth portion 11a.

Figure 10:
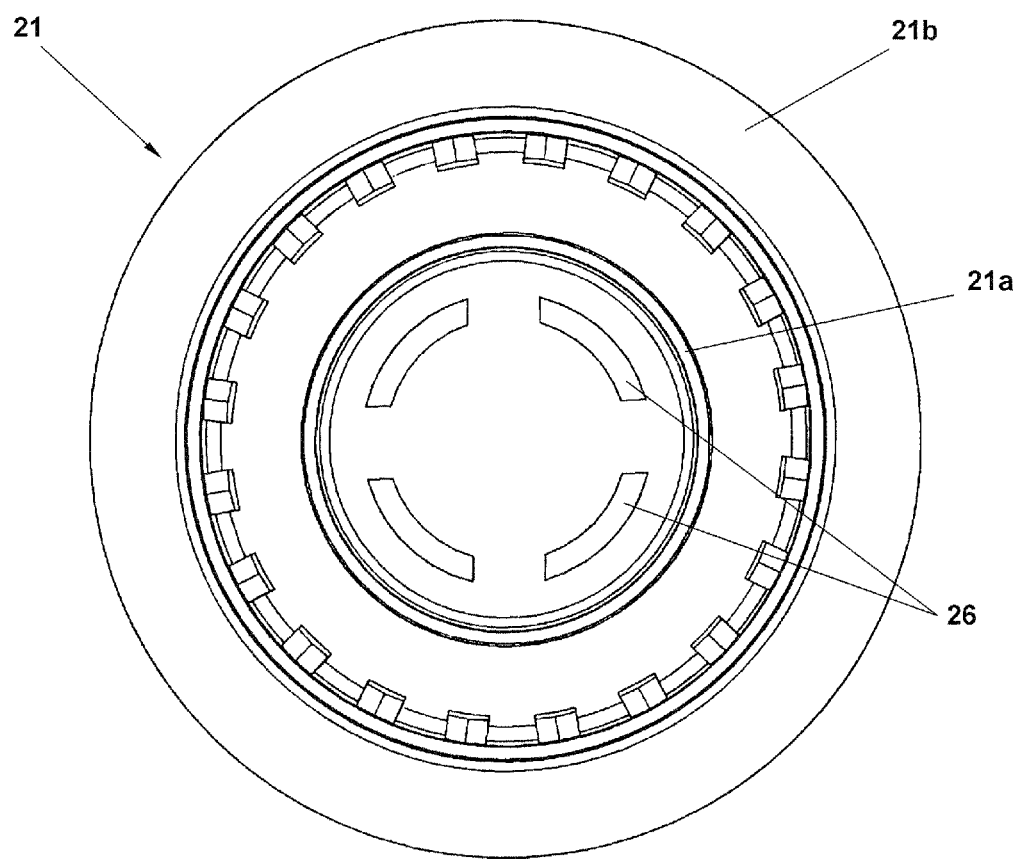
FIG. 10 is a bottom view of a base of the container.

The base 21 includes a damper wall 21e provided in the mouth portion 11a between the check valve 23 and the bottle body 11b. The damper wall 21e is provided integrally with the open end to close a lower end opening of the first tubular portion 21a, and spaced from the check valve 23 in the bottle. The damper wall 21e has liquid flow holes 26 each extending therethrough and having a smaller open area. In the illustrated embodiment, four liquid flow slits 26 each having a quarter arc shape are annularly arranged as also shown in FIG. 10.

The nozzle cap 22 is a generally cylindrical member. The top plate 22a is unitarily provided at an axially distal end of the nozzle cap 22. The nozzle portion 15 through which the liquid outlet port 13a extends is provided at the center of the top plate 22a. The nozzle cap 22 is fitted around the second and fourth tubular portions 21b, 21d of the base 21. The nozzle cap 22 has a cylindrical distal portion having a smaller diameter outer periphery with a step, and the protection cap 13 is threadingly engaged with the smaller diameter outer periphery.

The thin plate filter 25 is provided inside the top plate 22a of the nozzle cap 22. In order to prevent intrusion of outside air to prevent intrusion of bacteria, it is preferred to employ a hydrophilic porous planar filter as the filter 25. Alternatively, a membrane filter, a sintered filter, a hydrophobic porous planar filter or the like may be used as the filter 25 in the present invention. Even if the container has a construction free from the air lock, the prevention of the wetting of the filter before the first use of the container prevents proliferation of the bacteria the filter before the first use.

Figure 12:
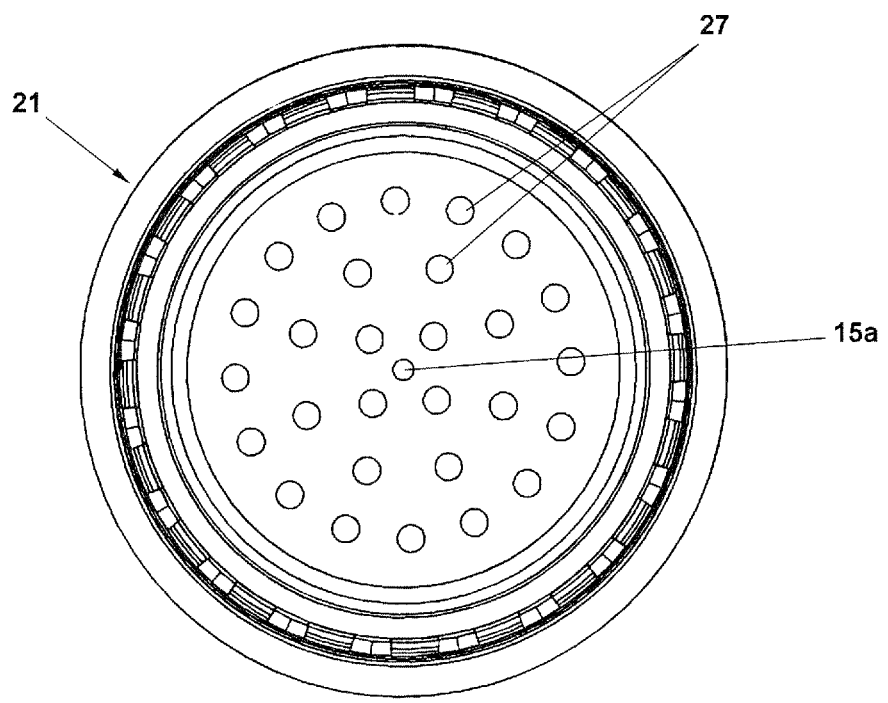
FIG. 12 is a bottom view of a nozzle cap of the container.

The filter 25 is disposed downstream of the check valve 23 with respect to the liquid discharging direction in the vicinity of a lower surface of the top plate 22a in the illustrated embodiment. The filter 25 is retained by the spacer 24 fitted in the fourth tubular portion 21d of the base 21. As also shown in FIG. 12, the top plate 22a has a plurality of projections 27 provided on the lower surface thereof to provide a flow passage through which the liquid flow to the outlet port 15a from a radially outward portion of the filter 25. The check valve 23 includes a valve flange 23c, a valve head 23b and a connector sleeve 23a, which are unitarily formed of an elastic material such as silicone rubber.

The valve flange 23c has a generally ring shape, and has a triangular cross section having a thickness that is progressively increased radially outward. The valve flange 23c is gas-tightly and liquid-tightly held between the spacer 24 and the base 21 from upper and lower sides, whereby an inner periphery of the discharge passage is gas-tightly and liquid-tightly sealed.

The valve head 23b has a round plan shape, and has a semispherical surface projecting inward of the bottle. The valve head 23b includes an orifice provided at the center thereof and having a cross-shaped incision. The orifice is opened to permit the liquid to flow from the inside of the inner layer bag 2 when a predetermined dispensing pressure is applied to an inner surface of the head 23b, and closed to block the flow of the liquid when the predetermined dispensing pressure is removed. The connector sleeve 23a has a generally cylindrical shape with its one axial end integrally connected to an inner peripheral edge of the valve flange 23c and with its other axial end integrally connected to an outer peripheral edge of the valve head 23b. The connector sleeve 23a has a relatively thin flexible structure so as to be easily deformable. When a predetermined pressure that is lower than the aforesaid predetermined dispensing pressure to be applied for opening the orifice is applied to the inner surface of the valve head 23b, the valve head 23b is displaced downstream (toward the distal end) with the orifice kept closed. As a result, the connector sleeve 23a is elastically deformed to be lifted. When the predetermined lower pressure is removed, the connector sleeve 23a recovers its original shape, whereby the valve head 23b is displaced upstream (toward the proximal end) with the orifice kept closed. As a result, a part of the liquid remaining in the liquid outlet port 15a is sucked back to the upstream side of the filter 25. A fluid suction force may be provided by the elastic recovery force of the connector sleeve 23a or by a negative pressure applied to the inner surface of the head 23b.

As also shown in FIGS. 2 to 8, the spacer 24 mainly includes a tubular body 24a fitted in the fourth tubular portion 21d of the base 21, a tubular valve support portion 24b projecting downward from a lower end of the main body 24a (adjacent to the check valve) into the third tubular portion 21c of the base 21, and a plurality of ribs 24c radially provided integrally with an upper end of the body 24a (adjacent to the filter). In this embodiment, four ribs are arranged in a cross shape. The ribs 24c each have a recessed groove which opens toward the check valve (downward in FIGS. 5 to 7) to serve as a liquid dam 14. The body 24a has a guide groove 16 provided in an inner peripheral wall thereof for guiding the liquid toward the dam 14 when the liquid percolates the closed check valve 23 and flows toward the filter 25 on the inner peripheral wall of the body 24a. In the illustrated embodiment, the guide groove 16 has a funnel shape or a valley shape which has a width progressively decreasing toward the dam 14.

Spaces defined between the ribs of the spacer 24 serve as liquid flow holes 17 through which the liquid flows from the check valve 23 to the filter 25. Thus, the discharge passage of the plug 12 through which the inside of the inner layer bag 2 of the bottle body 11b communicates with the outside of the container is defined collectively by the liquid flow holes 26 of the aforesaid base 21, the inner space of the first tubular portion 21a of the base, the inner space of the body 24a of the spacer, the liquid flow holes 17 of the spacer 24, an upper end cavity of the nozzle cap 22 and the liquid outlet port 15a. The discharging liquid flows from the open check valve up to and past the dam 14.

The present invention is not limited to the construction according to the embodiment described above, but may be arbitrarily modified within a technical scope defined by the scope of the claims. For example, the damper wall may be provided on a member attached to the bottle mouth portion separately from the base, or may be formed integrally with the bottle mouth portion. Further, the dam may be a cavity which substantially prevents the liquid flowing into the dam from flowing again out of the dam. The bottle may have a single-layer structure. The check valve is not limited to the suction valve employed in the above embodiment, but may be a valve which is not capable of sucking the liquid in the liquid outlet port of the distal nozzle. Further, the damper wall may abut against the check valve, or may be spaced from the check valve.

The invention claimed is:

1. A filtering dispenser container comprising:
a bottle having a body which contains a liquid, and a mouth portion through which the liquid is discharged from the body; and
a plug attached to the mouth portion of the bottle, having a discharge passage therein through which the liquid is discharged from the body of the bottle and including a filter and a check valve provided in the discharge passage, the check valve capable of being opened and closed, the filter being disposed downstream of the check valve with respect to a liquid discharging direction;
the container further comprising a dam provided between the check valve and the filter in the discharge passage for retaining the liquid percolating through the check valve with the check valve closed to prevent the filter from being wetted,
whereby liquid discharging from the open check valve flows up to and past the dam.

2. A filtering dispenser container as set forth in claim 1, wherein the plug further includes a spacer disposed between the check valve and the filter, and the spacer keeps the check valve and the filter a predetermined distance away from each other,
wherein the dam is provided in the spacer.

3. A filtering dispenser container as set forth in claim 1, wherein the dam is a groove which opens toward the check valve.

4. A filtering dispenser container as set forth in claim 1, wherein the discharge passage has a guide groove provided between the check valve and the dam in an inner peripheral wall thereof for guiding the liquid percolating through the closed check valve to the dam.

5. A filtering dispenser container as set forth in claim 1, further comprising a plurality of ribs radially provided between the check valve and the filter,
wherein the dam is provided in the ribs,
wherein liquid flow holes are defined between the ribs.

6. A filtering dispenser container as set forth in claim 1, further comprising a damper wall provided between the check valve and the body in the mouth portion,
wherein the damper wall has a liquid flow hole,
wherein the damper wall damps the flow of the liquid flowing therethrough.

7. A filtering dispenser container as set forth in claim 1, wherein the plug includes a tubular base liquid-tightly engaged with the mouth portion of the bottle, a nozzle cap liquid-tightly fitted around the base and having a liquid outlet port provided at a top thereof, and a tubular spacer fitted in the base downstream of the check valve with respect to the liquid discharging direction, the check valve being retained in the base, the filter being disposed between the top of the nozzle cap and the spacer,
wherein the dam is provided in the spacer, and the spacer has a liquid flow hole through which the liquid flows toward the filter after passing through the check valve when the check valve is open.

8. A filtering dispenser container as set forth in claim 7, wherein the spacer has a guide groove provided in an inner peripheral wall thereof for guiding the liquid percolating through the closed check valve to the dam.

9. A filtering dispenser container as set forth in claim 7, wherein the spacer has a plurality of ribs radially provided at an end thereof adjacent to the filter,
wherein the dam is provided in the ribs, and liquid flow holes are defined between the ribs.

10. A filtering dispenser container as set forth in claim 7, wherein the base includes a damper wall disposed between the check valve and the body in the mouth portion,
wherein the damper wall has a liquid flow hole, and damps the flow of the liquid flowing therethrough.

* * * * *